(12) United States Patent
Abe et al.

(10) Patent No.: US 7,842,185 B2
(45) Date of Patent: Nov. 30, 2010

(54) PELLETS COMPRISING SLUDGE CONTAINING NITRIFYING BACTERIA FOR TREATING WASTEWATER

(75) Inventors: Naoki Abe, Tokyo (JP); Koutarou Aoyama, Tokyo (JP); Tatsuo Sumino, Tokyo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 635 days.

(21) Appl. No.: 11/725,486

(22) Filed: Mar. 20, 2007

(65) Prior Publication Data

US 2007/0221571 A1 Sep. 27, 2007

(30) Foreign Application Priority Data

Mar. 23, 2006 (JP) ............................. 2006-081369

(51) Int. Cl.
  *C02F 3/00* (2006.01)
  *C12P 1/04* (2006.01)
  *C12N 11/04* (2006.01)
  *C12M 1/00* (2006.01)

(52) U.S. Cl. .................. 210/601; 435/170; 435/182; 435/289.1

(58) Field of Classification Search .................. None
  See application file for complete search history.

(56) References Cited

U.S. PATENT DOCUMENTS 4,791,061 A * 12/1988 Sumino et al. .............. 435/178
5,106,405 A * 4/1992 Goto ............................. 71/7
7,384,555 B1 * 6/2008 Yasui et al. ................ 210/605

FOREIGN PATENT DOCUMENTS

| JP | A-02-207894 | 8/1990 |
| JP | A-02207895 | 8/1990 |
| JP | A 09-000256 | 1/1997 |
| JP | A-11-090473 | 4/1999 |
| JP | A-11-033577 | 9/1999 |
| JP | B2 3131678 | 11/2000 |

OTHER PUBLICATIONS

Research Process for Environmental Microbial Engineering, p. 123, Gihodo Shuppan Co., Ltd. (1993).
Water Treatment by Microogranism Immobilization Process: Pellet Immobilization Process, Entrapping Immobilization Process, Biologically Activated Carbon Process, published by NTS Inc. (2000).
Standard Methods for Examination of Water, 2001 edition, Japan Water Works Association (2001).
Water Treatment Engineering, p. 204, Gihodo Shuppan Co., Ltd. (1976).

* cited by examiner

Primary Examiner—David M Naff
(74) Attorney, Agent, or Firm—Oliff & Berridge, PLC (57) ABSTRACT

Entrapping immobilization pellets in which microorganisms are entrapped and immobilized, the entrapping immobilization pellets comprising entrapped and immobilized purified water sludge containing nitrifying bacteria.

3 Claims, 7 Drawing Sheets

PELLETS COMPRISING SLUDGE CONTAINING NITRIFYING BACTERIA FOR TREATING WASTEWATER

BACKGROUND OF THE INVENTION

1. Field of the Invention

The present invention relates to entrapping immobilization pellets and a process for producing the same, and wastewater treatment process and equipment using the same. More particularly, the present invention relates to entrapping immobilization pellets that biologically denitrify ammonia from wastewater containing ammonia and a process for producing the same, and wastewater treatment process and equipment using the same.

2. Description of the Related Art

Nitrifying bacteria contained in activated sludge used for wastewater treatment grow slower than common bacteria. In particular, in winter during which water temperatures are low, such nitrifying bacteria have only a small number of bacterial cells and thus exhibit significantly reduced nitrification activity. This also applies to microorganisms having the same properties as in nitrifying bacteria.

In this situation, wastewater nitrification performance of nitrifying bacteria has been improved by immobilizing activated sludge containing nitrifying bacteria to the surface of an attachment material such as quartz sand, activated carbon, or plastic to increase the concentration of nitrifying bacteria (reference: Water Treatment by Microorganism Immobilization Process: Pellet Immobilization Process, Entrapping Immobilization Process, Biologically Activated Carbon Process, published by NTS Inc. in 2000).

However, the concentration of nitrifying bacteria cannot be sufficiently increased in attachment immobilization pellets in which microorganisms are attached to an attachment material, because the attached microorganisms are released from the material, or microorganisms differing from nitrifying bacteria as target microorganisms are attached to the material. Accordingly, wastewater has been treated at high speed with increased nitrification activity by producing entrapping immobilization pellets in which useful microorganisms such as nitrifying bacteria are entrapped and immobilized in an immobilizing material, and packing a reaction tank with the entrapping immobilization pellets to increase the concentration of nitrifying bacteria.

It is assumed that entrapping immobilization pellets have higher nitrification activity and can exhibit pellet performance earlier as the pellets have a larger number of nitrifying bacteria at the initial stage. Therefore, activated sludge containing nitrifying bacteria has conventionally been concentrated and then entrapped and immobilized in order to increase the number of nitrifying bacteria at the initial stage (reference: Research Process for Environmental Microbial Engineering, p. 123, Gihodo Shuppan Co., Ltd., published in 1993). Activated sludge refers to flocculated microorganisms grown by bubbling air to organic wastewater such as sewage, and the microorganisms include bacteria, fungi, protozoa, and micrometazoa. Organic substances in wastewater are adsorbed by bacteria and then taken and assimilated in the body, so that the bacteria are grown. The ecosystem is stable by the food chain in which the bacteria are through protozoa, micrometazoa, etc. (reference: Technology Seminar Text, The Actuality of Measures against Various Troubles in the Activated Sludge Process, Technical Information Center, Co., Ltd., July 2000). Activated sludge generally contains a large amount of organic substances in this manner.

Apart from entrapping immobilization pellets, there has been proposed a process for producing pellets having a large surface area on which useful microorganisms are supported (for example, Japanese Patent No. 3131678). The pellets are obtained by granulating purified water sludge mainly composed of inorganic components and then drying and burning the granules, and are supposed to result in porous microbial pellets having an extremely large specific area. There has also been proposed to mix sludge with useful microorganisms or cause microbial pellets to support useful microorganisms.

SUMMARY OF THE INVENTION

However, conventional entrapping immobilization pellets using activated sludge have drawbacks in that nitrifying bacteria cannot be stably grown, nitrification activity is slowly and unstably activated, and the pellets cannot sufficiently exhibit their inherent pellet performance. The main reasons for these drawbacks are as follows.

1) When entrapping immobilization pellets are produced by concentrating activated sludge, the number of heterotrophic bacteria contained in activated sludge other than nitrifying bacteria is also increased by the concentration, and heterotrophic bacteria other than the target bacteria may be dominant depending on the concentration conditions. Heterotrophic bacteria herein refer to all bacteria that form a colony in a medium containing a relatively low concentration of an organotroph when culturing the bacteria using the medium for a long time (20 to 28° C., 5 to 7 days) (Standard Methods for Examination of Water, 2001 edition, Japan Water Works Association, published in 2001).

2) Generally, activated sludge contains a large amount of organic substances and has a high VSS/SS of 0.7 to 0.9. Entrapping immobilization pellets using such activated sludge contain a large amount of organic substances. Heterotrophic bacteria are easily grown using the organic substances as substrates while consuming dissolved oxygen, and thus dissolved oxygen necessary for nitrification reaction tends to be insufficient.

3) Activated sludge forms a floc in which various microorganisms, mainly bacteria called zoogloea, are assembled, and the floc tends to adsorb organic substances in water (reference: Water Treatment Engineering, p. 204, Gihodo Shuppan Co., Ltd., published in 1976). Accordingly, heterotrophic bacteria are easily grown using organic substances adsorbed by the floc as substrates while consuming dissolved oxygen, and thus dissolved oxygen necessary for nitrification reaction tends to be insufficient.

4) Entrapping immobilization pellets produced are stored in a container for a certain period before use in a treatment tank. When the storage period is long, heterotrophic bacteria in the entrapping immobilization pellets consume dissolved oxygen. Thus, the inside of the entrapping immobilization pellets tends to be anaerobic, and methane fermentation tends to occur. When the pellets are anaerobic in this manner, dissolved oxygen necessary for nitrification reaction tends to be insufficient. Even if the entrapping immobilization pellets in such a state are used in an aerobic tank, nitrification activity is only slowly activated.

When methane fermentation occurs in the entrapping immobilization pellets, gas is easily pooled in the pellets, for example, and the strength and life of the entrapping immobilization pellets are decreased during storage of the pellets, unfavorably.

In the process of causing pellets to support useful microorganisms as in Japanese Patent No. 3131678, it is difficult to stably immobilize microorganisms on pellets, and the microorganisms may be released from the pellets, for example.

The present invention has been achieved in view of such circumstances. An object of the present invention is to provide entrapping immobilization pellets that have rapidly activated nitrification activity and stable pellet strength and a process for producing the same, and wastewater treatment process and equipment using the same.

According to a first aspect of the present invention, to attain the aforementioned object, there is provided entrapping immobilization pellets in which microorganisms are entrapped and immobilized, the entrapping immobilization pellets comprising entrapped and immobilized purified water sludge containing nitrifying bacteria.

Sludge generated in a water purification plant (purified water sludge) has been assumed to be free from nitrifying bacteria. Therefore, purified water sludge has not been used as seed sludge for entrapping and immobilizing nitrifying bacteria, and only activated sludge generated from a wastewater treatment plant has been used as seed sludge.

However, the present inventors have found that purified water sludge contains a large amount of inorganic substances and also contains microorganisms for natural purification such as nitrifying bacteria. The inventors have also found that entrapping immobilization pellets having nitrification activity more rapidly activated and pellet strength more stable than in conventional entrapping immobilization pellets can be obtained by applying such purified water sludge to entrapping immobilization pellets.

According to the first aspect, the entrapping immobilization pellets comprise entrapped and immobilized purified water sludge containing nitrifying bacteria. Thus, pellets can be obtained with rapidly activated nitrification activity and stable pellet strength.

The purified water sludge herein mainly refers to sludge obtained by purification treatment of river water, ground water, or dam lake water. Examples of the sludge include sludge collected when performing coagulation precipitation treatment in a water purification plant.

According to a second aspect of the present invention, there is provided the entrapping immobilization pellets according to the first aspect, wherein the purified water sludge has a VSS/SS of 0.1 to 0.3.

In the second aspect, a property of the purified water sludge is defined. According to the second aspect, the purified water sludge contained in the entrapping immobilization pellets has a VSS/SS of 0.1 to 0.3. Thus, pellets can be obtained with rapidly activated nitrification activity and stable pellet strength.

VSS/SS herein refers to a ratio of VSS (Volatile Suspended Solid, JIS K 0102 method) to SS (Suspended Solid, JIS K 0102 method), and is an index to show the content of organic substances in sludge.

According to a third aspect of the present invention, there is provided the entrapping immobilization pellets according to the first or second aspect, wherein the purified water sludge contained in the entrapping immobilization pellets has an average particle size of 10 μm to 30 μm.

According to the third aspect, the purified water sludge immobilized in the entrapping immobilization pellets has an average particle size of 10 μm to 30 μm, so that the pellet strength can be increased. Thus, pellets can be obtained with rapidly activated nitrification activity and stable strength.

Here, purified water sludge having an average particle size within the above range may be used as is. Purified water sludge having an average particle size outside the above range may also be used if the average particle size is controlled to be within such a range using a coagulant, a crushing device, or the like. The average particle size of purified water sludge specifically refers to an average particle size of particles containing silica or the like as a main component or particles in which microorganisms are coagulated. The average particle size of the purified water sludge can be readily measured by a laser diffraction/scattering particle size distribution analyzer.

According to a fourth aspect of the present invention, there is provided the entrapping immobilization pellets according to any one of the first to third aspects, wherein the entrapping immobilization pellets contains the purified water sludge for an SS concentration of 2 weight % or more.

According to the fourth aspect, the entrapping immobilization pellets contains the purified water sludge for an SS concentration of 2 weight % or more. Thus, pellets can be obtained with rapidly activated nitrification activity and stable strength. More preferably, the entrapping immobilization pellets contains the purified water sludge for an SS concentration of 2 weight % to 10 weight %.

According to a fifth aspect of the present invention, there is provided the entrapping immobilization pellets according to any one of the first to fourth aspects, wherein the entrapping immobilization pellets contains the purified water sludge for a VSS concentration of 0.2 weight % to 2 weight %.

The present inventors have found that the activation speed of nitrification activity differs depending on the concentration of organic substances contained in entrapping immobilization pellets. As a result of further extensive studies, the inventors have found an appropriate range of such a concentration.

According to the fifth aspect, the entrapping immobilization pellets contains the purified water sludge for a VSS concentration of 0.2 weight % to 2 weight %. Thus, nitrifying bacteria can be difficult to be affected by heterotrophic bacteria, and entrapping immobilization pellets can be obtained with rapidly activated nitrification activity and stable strength. More preferably, the entrapping immobilization pellets contains the purified water sludge for a VSS concentration of 0.5 weight % to 1 weight %.

According to a sixth aspect of the present invention, to attain the aforementioned object, there is provided entrapping immobilization pellets in which microorganisms are entrapped and immobilized, the entrapping immobilization pellets comprising entrapped and immobilized sludge containing nitrifying bacteria, the sludge having a VSS/SS of 0.1 to 0.3.

According to the sixth aspect, the entrapping immobilization pellets comprise entrapped and immobilized sludge containing nitrifying bacteria, and the sludge has a VSS/SS of 0.1 to 0.3. Thus, pellets can be obtained with rapidly activated nitrification activity and stable pellet strength.

In the sixth aspect, the sludge may be any sludge having the above composition other than purified water sludge, and may be culture sludge or lake sludge. The sludge used may be controlled to have a VSS/SS within the above range by introduction of purified water sludge, an inorganic coagulant, an inorganic substance, or the like into activated sludge.

According to a seventh aspect of the present invention, there is provided the entrapping immobilization pellets according to the sixth aspect, wherein the sludge contained in the entrapping immobilization pellets has an average particle size of 10 μm to 30 μm.

According to the seventh aspect, the sludge immobilized in the entrapping immobilization pellets has an average particle size of 10 μm to 30 μm, so that the pellet strength can be increased. Thus, pellets can be obtained with rapidly activated nitrification activity and stable strength.

When the sludge of the present invention has an average particle size within the above range, the sludge may be used for the entrapping immobilization pellets as is. Even when the sludge does not have an average particle size within the above range, the sludge may be used for the entrapping immobilization pellets after controlling the average particle size to be within the above range by use of a coagulant, a crushing device, or the like.

According to an eighth aspect of the present invention, there is provided the entrapping immobilization pellets according to the sixth or seventh aspect, wherein the entrapping immobilization pellets contains the sludge for an SS concentration of 2 weight % or more.

According to the eighth aspect, the sludge having a VSS/SS of 0.1 to 0.3 contained in the entrapping immobilization pellets for an SS concentration of 2 weight % or more. Thus, pellets can be obtained with more rapidly activated nitrification activity and more stable pellet strength. More preferably, the entrapping immobilization pellets contains the sludge for an SS concentration of 2 weight % to 10 weight %.

According to a ninth aspect of the present invention, there is provided the entrapping immobilization pellets according to any one of the sixth to eighth aspects, wherein the entrapping immobilization pellets contains the sludge for a VSS concentration of 0.2 weight % to 2 weight %.

According to the ninth aspect, the entrapping immobilization pellets contains the sludge for a VSS concentration of 0.2 weight % to 2 weight %. Thus, entrapping immobilization pellets can be obtained with rapidly activated nitrification activity and stable strength. More preferably, the entrapping immobilization pellets contains the sludge for a VSS concentration of 0.5 weight % to 1 weight %.

According to a tenth aspect of the present invention, to attain the aforementioned object, there is provided a process for producing entrapping immobilization pellets, comprising mixing purified water sludge containing nitrifying bacteria with an immobilizing material and gelling the mixture to entrap and immobilize the purified water sludge as seed sludge for the nitrifying bacteria.

According to an eleventh aspect of the present invention, to attain the aforementioned object, there is provided a process for producing entrapping immobilization pellets, comprising mixing sludge containing nitrifying bacteria and having a VSS/SS of 0.1 to 0.3 with an immobilizing material, so that the entrapping immobilization pellets contains the sludge for an SS concentration of 2 weight % or more, and gelling the mixture to entrap and immobilize the sludge.

The tenth and eleventh aspects show the process for producing entrapping immobilization pellets according to the present invention.

According to a twelfth aspect of the present invention, there is provided a wastewater treatment process comprising introducing the entrapping immobilization pellets according to any one of the first to ninth aspects into a treatment tank to treat wastewater.

According to a thirteenth aspect of the present invention, there is provided wastewater treatment equipment comprising the entrapping immobilization pellets according to any one of the first to ninth aspects in a treatment tank.

According to the twelfth and thirteenth aspect, wastewater is treated in wastewater treatment equipment comprising the entrapping immobilization pellets of the present invention in a treatment tank (such as an aerobic tank). Thus, wastewater can be treated stably and rapidly.

According to the present invention, entrapping immobilization pellets can be obtained with rapidly activated nitrification activity and stable pellet strength.

DETAILED DESCRIPTION OF THE PREFERRED EMBODIMENTS

Preferred embodiments of the entrapping immobilization pellets and the process for producing the same, and the wastewater treatment process and equipment using the same according to the present invention will be described below with reference to the accompanying drawings.

Figure 1:
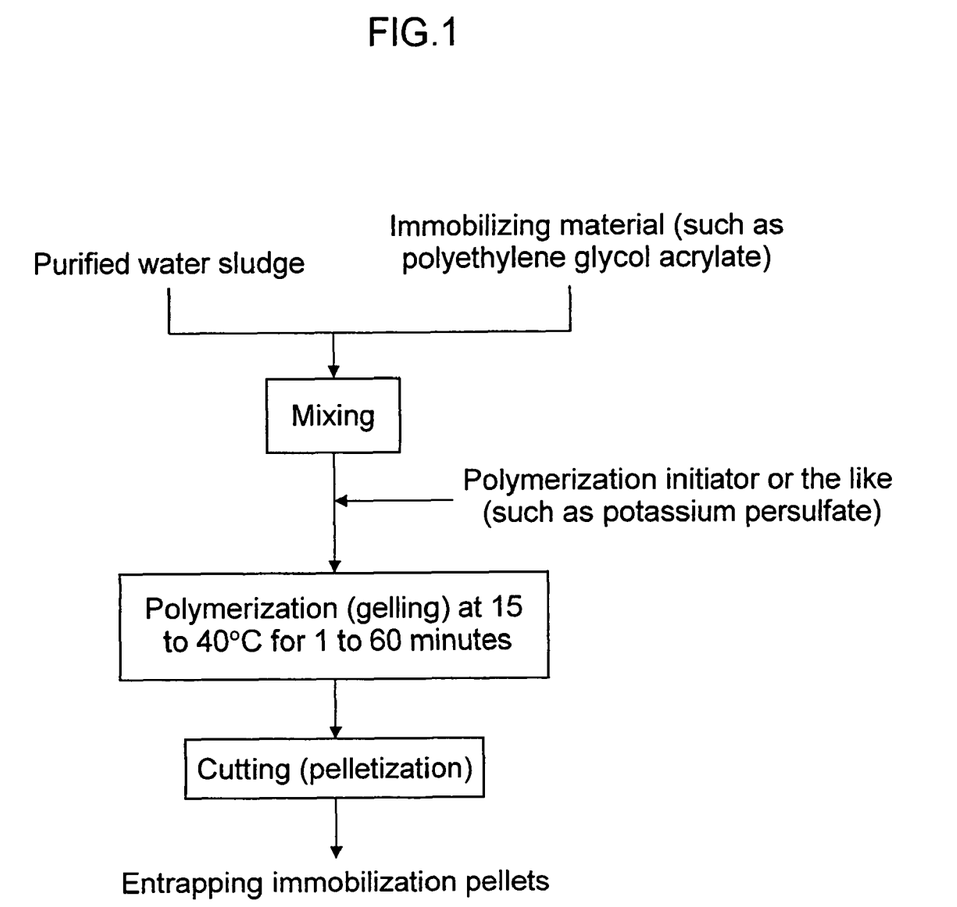
FIG. 1 is a view showing an example of the process for producing entrapping immobilization pellets according to the present invention.

FIG. 1 is a view showing an example of the process for producing entrapping immobilization pellets according to the present invention. As shown in FIG. 1, purified water sludge containing microorganisms is first mixed with an immobilizing material to prepare a raw material liquid. Next, a polymerization initiator such as potassium persulfate is added to the raw material liquid, and the mixture is polymerized (gelled) at a polymerization temperature of 15 to 40° C., and preferably 20 to 30° C., for a polymerization time of 1 to 60 minutes, and preferably 1.5 to 60 minutes. Then, the gelled pellet sheet is cut into about 3 mm-square angular pellets. The entrapping immobilization pellets of the present invention are thus produced.

The purified water sludge mainly refers to sludge obtained by purification treatment of river water, ground water, or dam lake water. Examples of the sludge include sludge collected from a water purification plant. The water source for a water purification plant is not specifically limited to the above-mentioned rivers, ground water, or dam lakes.

The purified water sludge is composed of natural sand grains containing aluminum or the like by addition of a coagulant. The sludge mainly contains a large amount of inorganic components and further contains bacteria for natural purification (such as nitrifying bacteria). The coagulant used may be a coagulant generally used such as aluminum-based sulfuric acid band, polyaluminum chloride (PAC), ferric chloride, or polyferric sulfate, and is not specifically limited.

The purified water sludge has a VSS/SS of preferably 0.1 to 0.3, and more preferably 0.15 to 0.25. When the purified water sludge does not have a VSS/SS within the above range, the VSS/SS can be controlled by adding an inorganic substance, activated sludge, or an organic substance to the purified water sludge, by burning a part of the purified water sludge, or by diluting the sludge, for example.

The sludge used in the present embodiment is not limited to the above-described purified water sludge. It is also possible to use other sludges (such as culture sludge and lake sludge) having a VSS/SS of 0.1 to 0.3. Activated sludge typically has a VSS/SS of 0.7 to 0.9. It is also possible to use such activated sludge controlled to have a VSS/SS within the above range by addition of purified water sludge, an inorganic coagulant, an inorganic substance, or the like to the activated sludge.

The purified water sludge, or sludge having a VSS/SS of 0.1 to 0.3 (hereinafter generally referred to as "purified water sludge or the like") preferably contains microorganisms for natural purification, in particular, complex microorganisms such as nitrifying bacteria, denitrifying bacteria, or anaerobic ammonium oxidizing bacteria.

The purified water sludge or the like has an average particle size of preferably 10 µm to 30 µm, and more preferably 10 µm to 20 µm. Because this allows the sludge itself to be uniformly dispersed in the entrapping immobilization pellets, the pellet strength can be increased. The purified water sludge or the like can be uniformly mixed with the immobilizing material due to its high affinity to the immobilizing material.

When the purified water sludge or the like has an average particle size within the above range, the sludge may be used for the entrapping immobilization pellets as is. Even when the purified water sludge or the like does not have an average particle size within the above range, the sludge may be used for the entrapping immobilization pellets after controlling the average particle size to be within the above range by use of a coagulant or a crushing device (such as a homogenizer). The coagulant used may be a coagulant generally used such as aluminum-based sulfuric acid band, polyaluminum chloride (PAC), ferric chloride, or polyferric sulfate, as in the case described above.

The purified water sludge or the like has a viscosity lower than that of activated sludge. For example, the purified water sludge having an SS concentration of 10,000 mg/L has a viscosity of preferably 5 mPa·s to 30 mPa·s (20° C.), and more preferably 5 mPa·s to 15 mPa·s (20° C.). The viscosity of the purified water sludge or the like can be controlled by mixing the sludge with a solvent such as water or low-viscosity sludge to dilute the sludge, by adding a thickener to the sludge, or by concentrating the sludge.

The entrapping immobilization pellets contains the purified water sludge or the like for an SS concentration of preferably 2 weight % or more, and more preferably 2 weight % to 10 weight %. The SS concentration of the purified water sludge or the like to the entrapping immobilization pellets in the entrapping immobilization pellets can be controlled by adding an inorganic substance to the purified water sludge or diluting or concentrating the sludge as described above.

The entrapping immobilization pellets contains the purified water sludge or the like for a VSS concentration of preferably 0.2 weight % to 2 weight %, and more preferably 0.5 weight % to 1 weight %. The VSS concentration of the purified water sludge or the like to the entrapping immobilization pellets, in the entrapping immobilization pellets can be controlled by adding an organic substance to the purified water sludge or diluting or concentrating the sludge as described above.

The purified water sludge or the like may be used alone or in any combination with other sludges, microorganisms, or the like.

The immobilizing material may be a high-molecular-weight monomer, prepolymer, oligomer, or the like, but is not specifically limited. For example, a polyethylene glycol polymer, a polyvinyl alcohol polymer, or the like is preferably used. Specifically, a prepolymer having a molecular weight of 4,000 which contains ethylene oxide and propylene oxide at 7:3 and has a diacrylate as a terminal group may be preferably used.

Further, polyethylene glycol acrylate, polyethylene glycol diacrylate, polyethylene glycol methacrylate, or the like may be used as the immobilizing material. In addition, the following prepolymers may also be used:

monomethacrylates such as polyethylene glycol monomethacrylate, polyprene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate; monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate;

dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane;

trimethacrylates such as trimethylolpropane trimethacrylate;

triacrylates such as trimethylolpropane triacrylate, pentaerythritol triacrylate, trimethylolpropane EO-added triacrylate, glycerol PO-added triacrylate, and ethoxylated trimethylolpropane triacrylate;

tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate; and other prepolymers such as acrylamide, acrylic acid, and dimethylacrylamide.

The immobilization materials may be used singly or in a combination of two or more.

In the present embodiment, polymerization of the entrapping immobilization pellets is most appropriately radical polymerization using potassium persulfate, but may be polymerization using ultraviolet rays or electron beams or redox polymerization. In radical polymerization using potassium persulfate, potassium persulfate is preferably added in an amount of 0.001 weight % to 0.25 weight %, and an amine polymerization promoter is preferably added in an amount of 0.001 weight % to 0.5 weight % as β-dimethylaminopropionitrile, N,N,N',N'-tetramethylethylenediamine, or the like. Sodium sulfite can also be preferably used. These polymerization initiators or polymerization promoters may be used singly or in a combination of two or more.

In the present embodiment, sheet forming is used as a process for forming entrapping immobilization pellets, but the process is not limited thereto. Tube forming, drop granulation, block forming, or the like may also be used.

The entrapping immobilization pellets produced in the above manner are preferably subjected to activation (acclimatization) before full-scale operation of wastewater treatment. The entrapping immobilization pellets are preferably activated by a process of bringing real wastewater or synthetic wastewater containing ammonia and nitrite into contact with the entrapping immobilization pellets.

Figure 2:
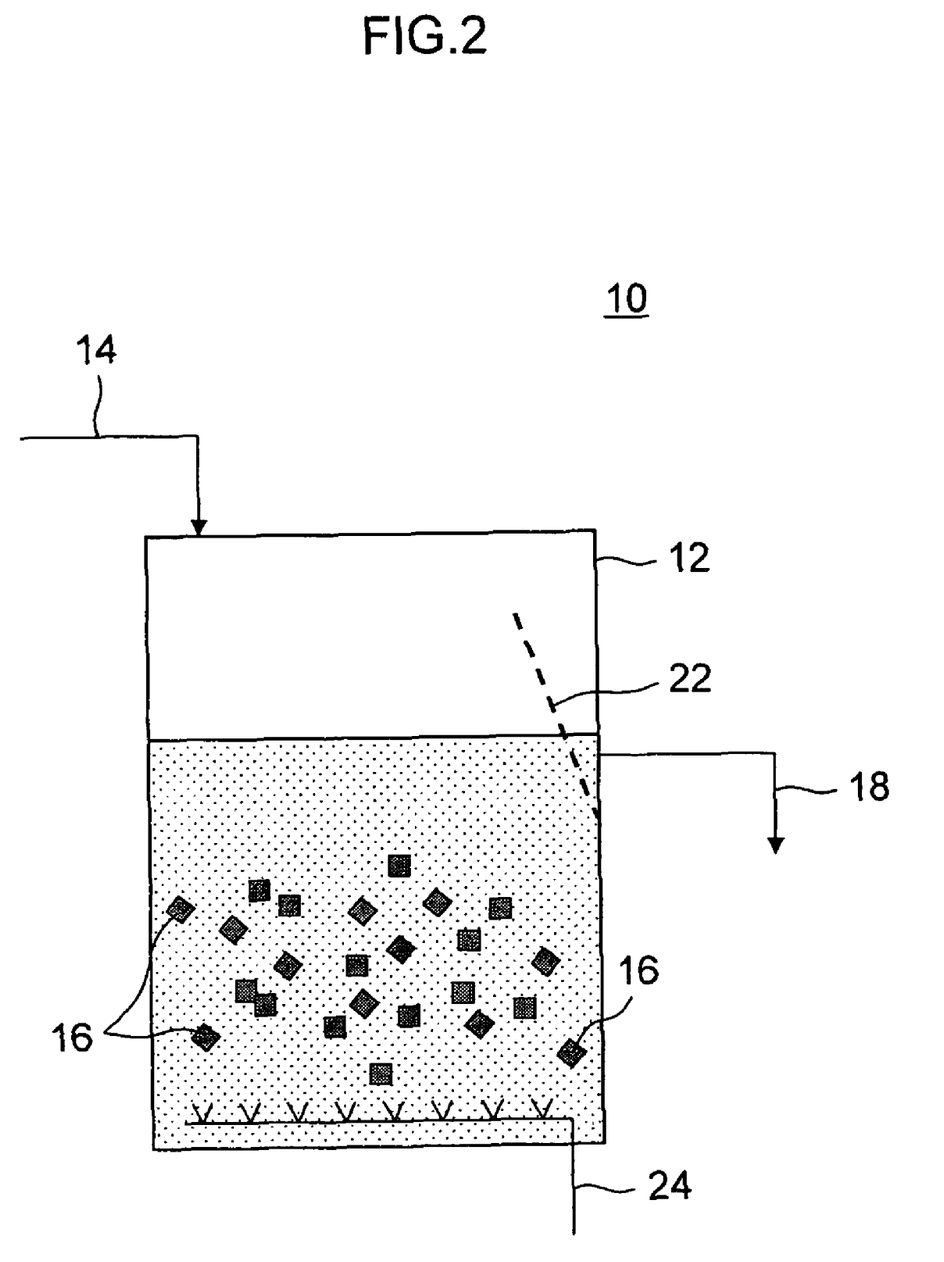
FIG. 2 is a view describing an example of the wastewater treatment equipment 10 of the present embodiment.

Next, an example of applying the entrapping immobilization pellets to wastewater treatment for removing nitrogen will be described. FIG. 2 is a view describing an example of wastewater treatment equipment 10 using the entrapping immobilization pellets of the present invention.

As shown in FIG. 2, the wastewater treatment equipment 10 has, as main components, a treatment tank 12 for treating raw water; an inflow pipe 14 of allowing raw water containing ammonia to flow into the treatment tank 12; entrapping immobilization pellets 16 of the present invention introduced into the treatment tank 12; and a discharge pipe 18 of discharging the treated water from the treatment tank 12.

The treatment tank 12 is an apparatus that includes the entrapping immobilization pellets 16 and treats raw water containing ammonia flown from the inflow pipe 14 to remove ammonia. A screen 22 for suppressing discharge of the entrapping immobilization pellets 16 is provided near the discharge port of the treatment tank 12. A diffuser pipe 24 for bubbling air necessary for nitrification reaction is provided in the treatment tank 12.

The packing ratio of the entrapping immobilization pellets 16 in the treatment tank 12 is preferably 5 vol % to 40 vol %, and more preferably 8 vol % to 20 vol %. The packing ratio of attachment pellets is preferably 40 vol % to 90 vol %, and more preferably 50 vol % to 80 vol %.

In such a configuration, raw water containing ammonia is flown into the treatment tank 12 from the inflow pipe 14, and nitrification reaction is carried out by microorganisms (such as nitrifying bacteria) in the entrapping immobilization pellets 16 of the present invention, so that ammonia in the raw water is oxidized into nitrite or nitrate. Air necessary for the nitrification reaction is supplied from the diffuser pipe 24. The treated water is discharged from the discharge pipe 18 through the screen 22.

Wastewater can be stably treated by packing the treatment tank 12 with the entrapping immobilization pellets 16 of the present invention in this manner. The pellets have activity rapidly activated, and the treatment time can be significantly reduced.

According to the entrapping immobilization pellets and the process for producing the same, and the wastewater treatment process and equipment using the same according to the present invention, entrapping immobilization pellets can be obtained with rapidly activated nitrification activity and stable pellet strength.

Embodiments of the entrapping immobilization pellets and the process for producing the same, and the wastewater treatment process and equipment using the same according to the present invention are as described above. However, the present invention is not limited to the above embodiments, and various embodiments are possible.

For example, in the present embodiment described above, the entrapping immobilization pellets contain nitrifying bacteria. However, the present embodiment can be applied to entrapping immobilization pellets containing microorganisms difficult to be grown other than nitrifying bacteria.

The sludge of the present invention (such as purified water sludge) can be used not only for entrapping immobilization pellets but also as microorganisms or sludge for other microbial pellets (such as attachment immobilization pellets, contact filters, or pellets having a biofilm formed).

EXAMPLE

Next, the present invention will be described in detail with reference to the example. However, the present invention is not limited to the following example.

1) Type of Sludge

Entrapping immobilization pellets having different types of sludge were prepared to compare the nitrification performance.

(Materials for Entrapping Immobilization Pellets)

Type of sludge: Purified water sludge (VSS/SS=0.198) (Test 1), lake sludge (Test 2), activated sludge (Test 3), anaerobic sludge (Test 4)

Sludge concentration in the pellets: 2 weight %-pellet

Immobilizing material: Polyethylene glycol diacrylate, 5 weight %

Polymerization promoter: N,N,N',N'-tetramethylethylenediamine, 0.0500 weight %

Polymerization initiator: Potassium persulfate, 0.0025 weight %

Each of the four types of sludge was mixed with the immobilizing material, polymerization initiator, and polymerization promoter to carry out radical polymerization at a polymerization temperature of 20° C. for 30 minutes, and then the polymer was formed into four types of about 3 mm-square entrapping immobilization pellets. Sludge in a methane fermentation tank was used as the anaerobic sludge.

(Wastewater Treatment Conditions)

Wastewater used: Inorganic synthetic wastewater (containing 40 mg/L of ammonium nitrogen)

Volume of treatment tank 12: 2 L

Packing ratio of entrapping immobilization pellets 16: 10%

Diffused volume: 2 L/(L·min)

Retention time: Three hours

Treatment temperature: 20° C.

The four types of entrapping immobilization pellets were respectively subjected to wastewater treatment (acclimatization) under the above treatment conditions. The nitrification speed of the pellets was calculated by measuring the amounts of ammonium nitrogen in the inflow wastewater and in the treated water and determining the amount of reduced ammonium nitrogen. The results at that time are shown in FIG. 3.

Figure 3:
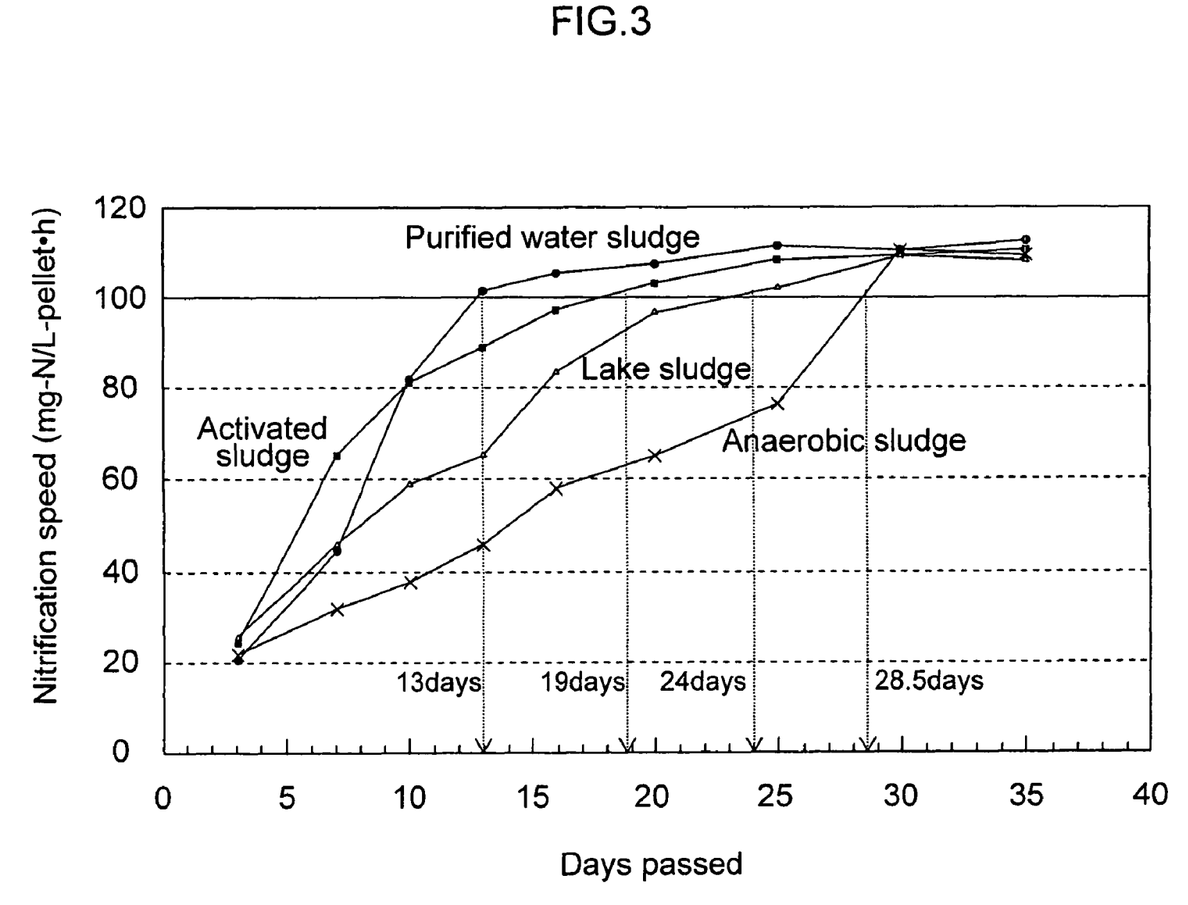
FIG. 3 is a graph in the present example.

As shown in FIG. 3, the number of days necessary for achieving a nitrification speed of the pellets of 100 mg-N/L-pellet·h was smallest and 13 days for the pellets using purified water sludge (Test 1).

On the other hand, such a number of days was 19 days for the pellets using activated sludge (Test 3), 24 days for the pellets using lake sludge (Test 2), and 28.5 days for the pellets using anaerobic sludge (Test 4), all of which were larger than in the pellets using purified water sludge (Test 1). From this it was found that entrapping immobilization pellets using purified water sludge have nitrification activity most rapidly activated.

Next, the number of nitrifying bacteria contained in each type of the entrapping immobilization pellets was measured by the MPN (Most Probable Number) method in order to examine that the above results were based on the number of nitrifying bacteria.

The pellet strength was also measured for each type of the entrapping immobilization pellets. The pellet strength of the entrapping immobilization pellets (MPa/cm$^2$) was calculated by measuring using a rheometer the pressure (kg) gradually applied to the pellet surface enough to break the pellets, and dividing the pressure by the cross-sectional area of the pellets (cm$^2$). The results are shown in Table 1.

TABLE 1

| Type of sludge | Number of nitrifying bacteria (cells/mL-pellet) | Pellet strength (Mpa/cm$^2$) |
| --- | --- | --- |
| Test 1 | Purified water sludge | 6 × 10$^3$ | 0.72 |
| Test 2 | Lake sludge | 2 × 10$^2$ | 0.32 |
| Test 3 | Activated sludge | 2 × 10$^5$ | 0.51 |
| Test 4 | Anaerobic sludge | 8 × 10$^2$ | 0.35 |

As shown in Table 1, the number of nitrifying bacteria contained in the entrapping immobilization pellets is larger in the order of activated sludge, purified water sludge, anaerobic sludge, and lake sludge. Thus, it was confirmed that the time necessary for activating nitrification activity described above (FIG. 3) is not necessarily proportional to the number of nitrifying bacteria. Nitrifying bacteria of purified water sludge were rapidly grown in this manner, presumably because a floc was not formed as in activated sludge, making the amount of organic substances adsorbed small, and the concentration of organic substances in the pellets was low, so that there was an environment in which heterotrophic bacteria were difficult to be grown and nitrifying bacteria were easily grown.

The entrapping immobilization pellets using purified water sludge (Test 1) had a highest pellet strength which was about 1.4 times the pellet strength of conventional activated sludge.

2) Composition of Purified Water Sludge (VSS/SS)

Next, the relation between the composition of purified water sludge and nitrogen removal performance was examined. In the present example, two types of purified water sludge having a composition shown in Table 2 and activated sludge for comparison were used.

(Composition of Sludge)

TABLE 2

| Type of sludge | Purified water sludge P | Purified water sludge Q | Activated sludge |
| --- | --- | --- | --- |
| SS (mg/L)*$^1$ | 81000 | 36000 | 29000 |
| VSS (mg/L)*$^2$ | 16000 | 6400 | 23000 |
| VSS/SS (%) | 19.8 | 17.8 | 79.3 |
| Al content (%-against SS) | 9.5 | 9.4 | 1.1 |
| Fe content (%-against SS) | 7.7 | 3.2 | 0.4 |

*$^1$SS: Floated or suspended substances including inorganic substances and organic substances.
*$^2$VSS: SS volatilized upon ignition, mainly organic substances.

As shown in Table 2, the purified water sludges P or Q had a content of organic substances VSS/SS extremely lower than that of the activated sludge. On the contrary, the purified water sludges P or Q had a content of inorganic substances (Al and Fe) higher than that of the activated sludge.

Entrapping immobilization pellets shown in Table 3 were produced in the same manner as in 1) using the sludges shown in Table 2.

TABLE 3

| | Type of sludge | SS concentration in sludge of the pellets (mg/L) |
| --- | --- | --- |
| Test 1 | Purified water sludge P | 54000 |
| Test 2 | Purified water sludge Q | 20000 |
| Test 3 | Activated sludge | 20000 |

The wastewater treatment test was carried out for each type of the entrapping immobilization pellets shown in Table 3 under the same conditions as in the above 1) to measure the ammonium nitrogen concentration in the treated water with respect to the days passed. The results are shown in FIGS. 4A and 4B.

Figure 4A:
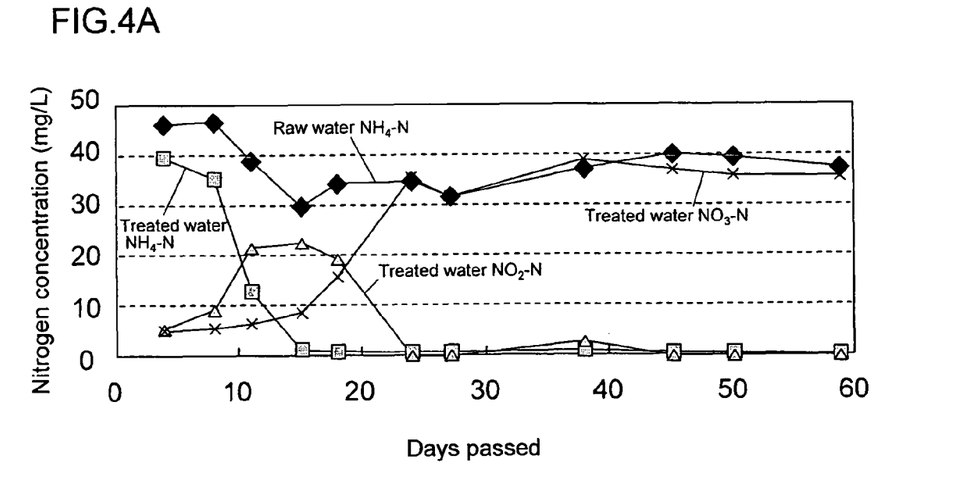
FIGS. 4A and 4B are graphs in the present examples.
Figure 4B:
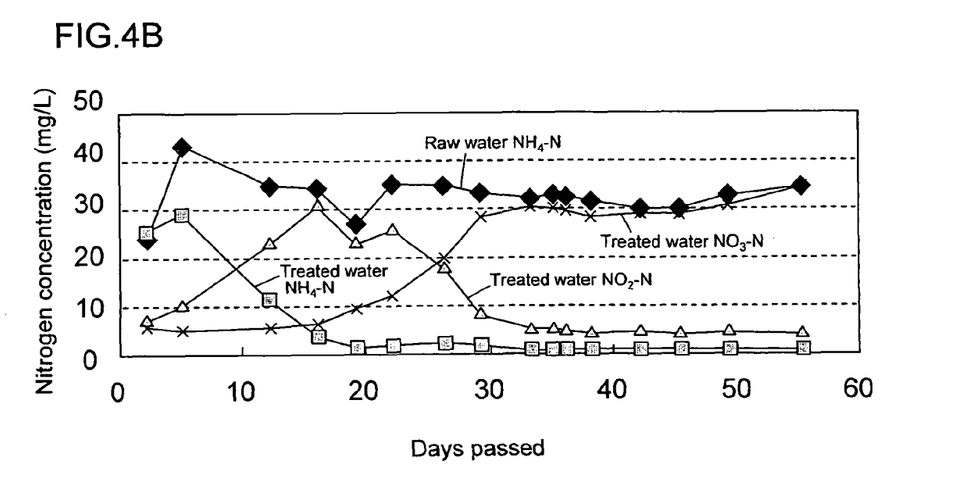

As shown in FIG. 4A, in Test 1 using the purified water sludge P, ammonium nitrogen in the treated water was almost completely removed after 15 days had passed. Likewise, as shown in FIG. 4B, in Test 2 using the purified water sludge Q, ammonium nitrogen in the treated water was almost completely removed after 20 days had passed.

On the contrary, in Test 3 using conventional activated sludge, it took 28 days to almost completely remove ammonium nitrogen in the treated water.

As described above, it was found that conventional activated sludge needs a considerably longer time to remove ammonium nitrogen in treated water as compared with the purified water sludge of the present invention used in Tests 1 and 2. From this it was found that entrapping immobilization pellets using the purified water sludge can significantly reduce the time for activating nitrogen removal performance.

3) Average Particle Size of Purified Water Sludge

Next, entrapping immobilization pellets using purified water sludge were examined for the relation between the average particle size of the purified water sludge and the pellet strength of the entrapping immobilization pellets.

In the present example, the purified water sludge in the above 1) was used as the purified water sludge. The average particle size of the purified water sludge was controlled by addition of a coagulant or use of a homogenizer. Except for such conditions, the same conditions as in the above 1) were used for preparing the entrapping immobilization pellets.

The pellet strength of the entrapping immobilization pellets (MPa/cm$^2$) was calculated by measuring using a rheometer the pressure (kg) gradually applied to the pellet surface enough to break the pellets, and dividing the pressure by the cross-sectional area of the pellets (cm$^2$) in the same manner as described above. The results are shown in FIG. 5.

Figure 5:
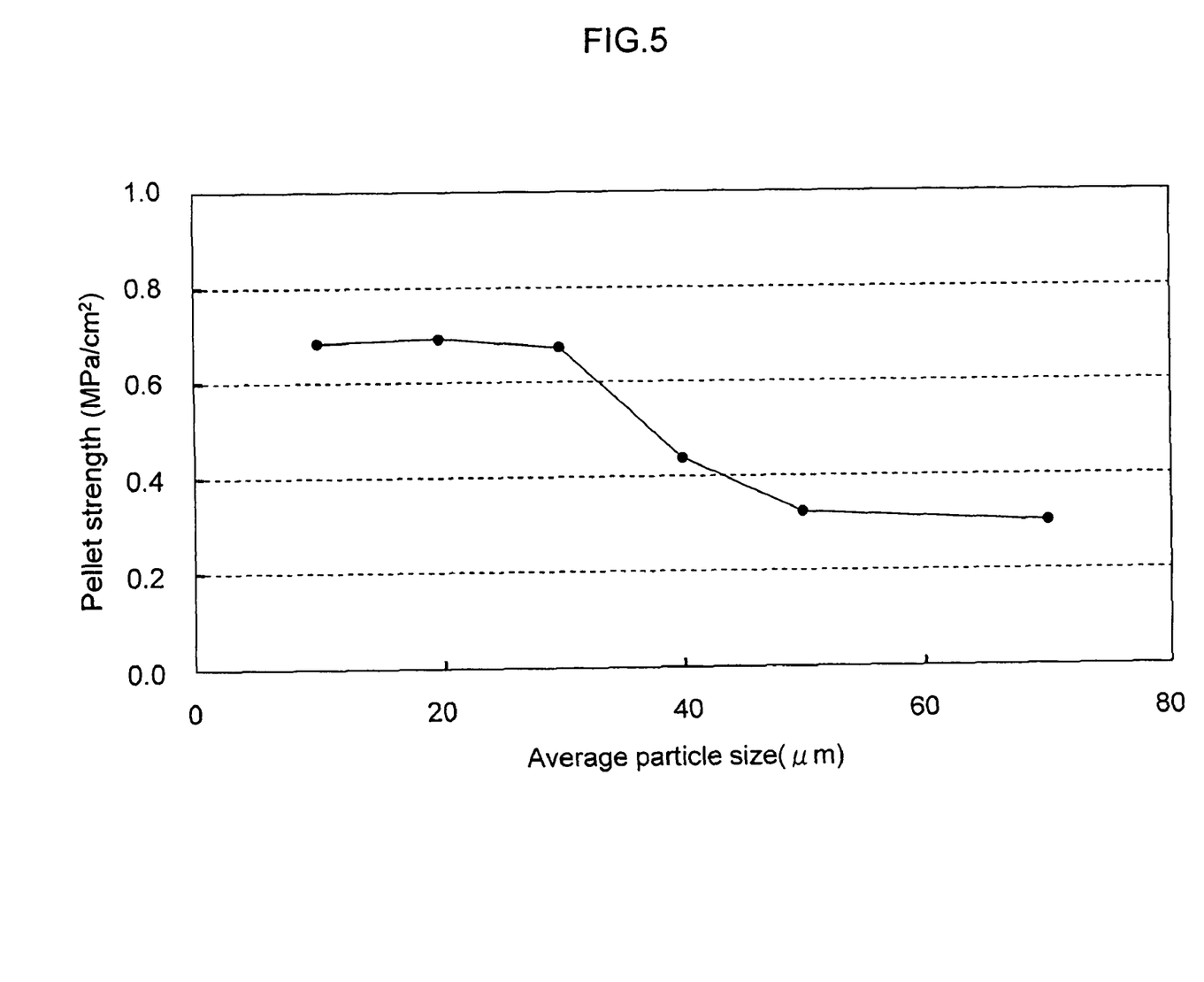
FIG. 5 is a graph in the present example.

As shown in FIG. 5, when the purified water sludge had an average particle size of 30 μm or less, the pellet strength was almost constant and high. However, it was found that the pellet strength was gradually decreased when the average particle size was more than 30 μm. Presumably, a reason for this is that the purified water sludge acts as a filler. It was found that pellets using the purified water sludge can have a strength about 1.4 times higher than that of pellets using conventional activated sludge.

Further, it was difficult to control the average particle size of the purified water sludge to less than 10 μm. From this it was found that the purified water sludge preferably has an average particle size of 10 μm to 30 μm.

4) SS Concentration of Purified Water Sludge to Entrapping Immobilization Pellets, in Entrapping Immobilization Pellets Next, entrapping immobilization pellets using purified water sludge were examined for the relation between the SS concentration of the purified water sludge to the entrapping immobilization pellets, in the pellets and the nitrification speed.

In the present example, entrapping immobilization pellets were prepared under the same conditions as in the above 1) so that the pellets contained the purified water sludge for an SS concentration of 1 weight % to 6 weight %.

(Wastewater Treatment Conditions)

Wastewater used: Inorganic synthetic wastewater (containing 40 mg/L of ammonium nitrogen)

Volume of treatment tank 12: 2 L

Packing ratio of entrapping immobilization pellets 16: 10%

Diffused volume: 2 L/(L·min)

Retention time: Three hours

Treatment temperature: 20° C.

The entrapping immobilization pellets were respectively subjected to wastewater treatment (acclimatization) under the above treatment conditions. The nitrification speed of the pellets was measured after two weeks had passed at 20° C. The nitrification speed of the pellets was measured by a batch test using inorganic synthetic wastewater. The results at that time are shown in FIG. 6.

Figure 6:
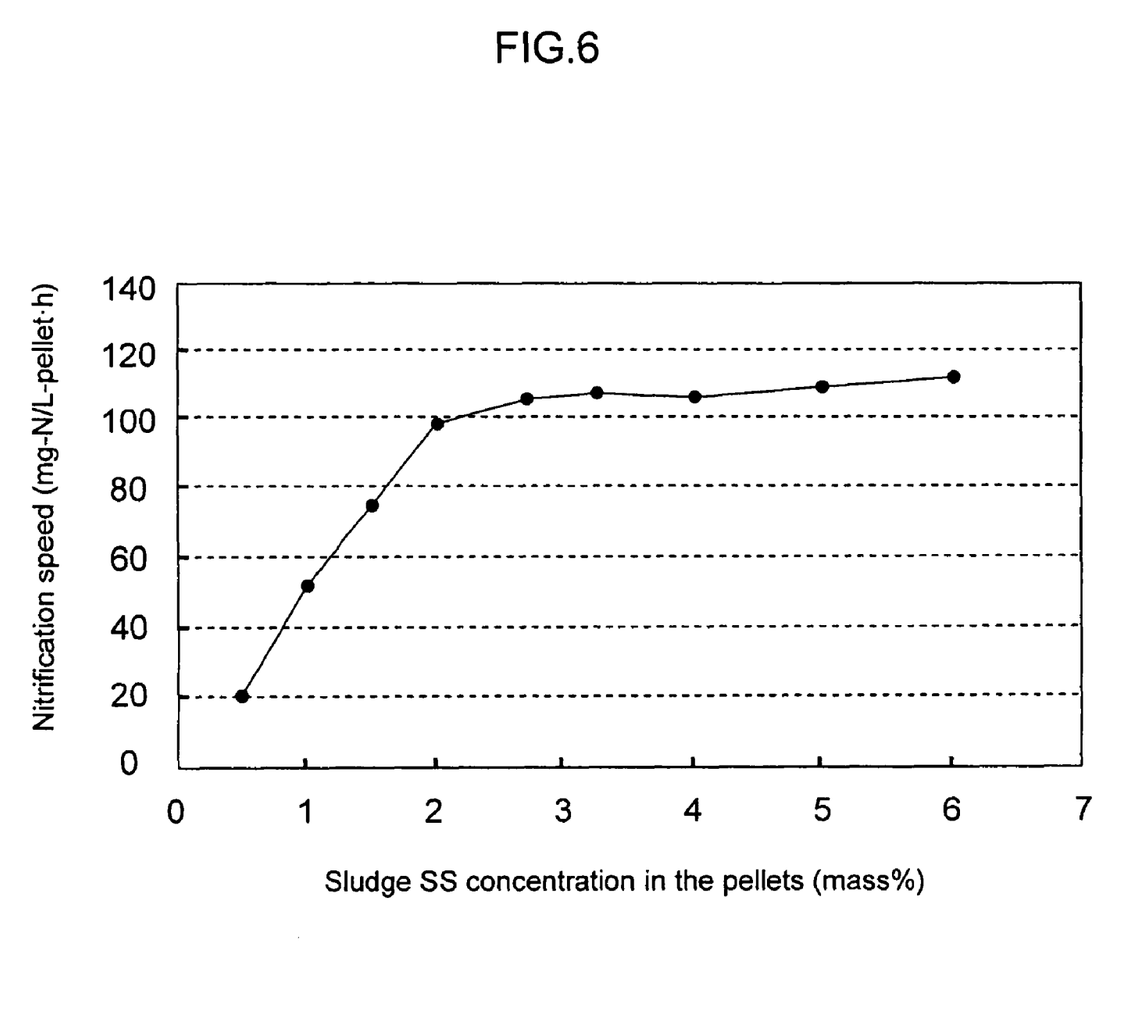
FIG. 6 is a graph in the present example.

As shown in FIG. 6, the nitrification speed was increased as the SS concentration of the purified water sludge to the entrapping immobilization pellets, in the pellets was increased, and the nitrification speed was stable to be an almost constant value when the pellets contained the purified water sludge for an SS concentration of 2 weight % or more. From this it was found that the concentration of nitrifying bacteria is high and nitrification reaction is rapidly activated when the pellets contained the purified water sludge for an SS concentration of 2 weight % or more.

5) VSS Concentration of Purified Water Sludge to Entrapping Immobilization Pellets, in Entrapping Immobilization Pellets Next, entrapping immobilization pellets using purified water sludge were examined for the relation between the VSS concentration of the purified water sludge to the entrapping immobilization pellets, in the pellets and the increasing rate of nitrifying bacteria.

In the present example, the purified water sludge in the above 1) was used as the purified water sludge. The VSS concentration of the purified water sludge to the entrapping immobilization pellets, in the pellets was controlled by adding sterile activated sludge to sterile purified water sludge.

The entrapping immobilization pellets were prepared using cultured nitrifying bacteria as the nitrifying bacteria so that the number of nitrifying bacteria was 40,000 cells/mL-pellet. Except for such conditions, the same conditions as above were used for preparing the entrapping immobilization pellets.

The increasing rate of nitrifying bacteria in the pellets was measured after two weeks had passed at 20° C. The increasing rate of nitrifying bacteria referred to a ratio of the number of nitrifying bacteria two weeks after acclimatization to the number of nitrifying bacteria before acclimatization. The number of nitrifying bacteria was measured by the MPN method. The results are shown in FIG. 7.

Figure 7:
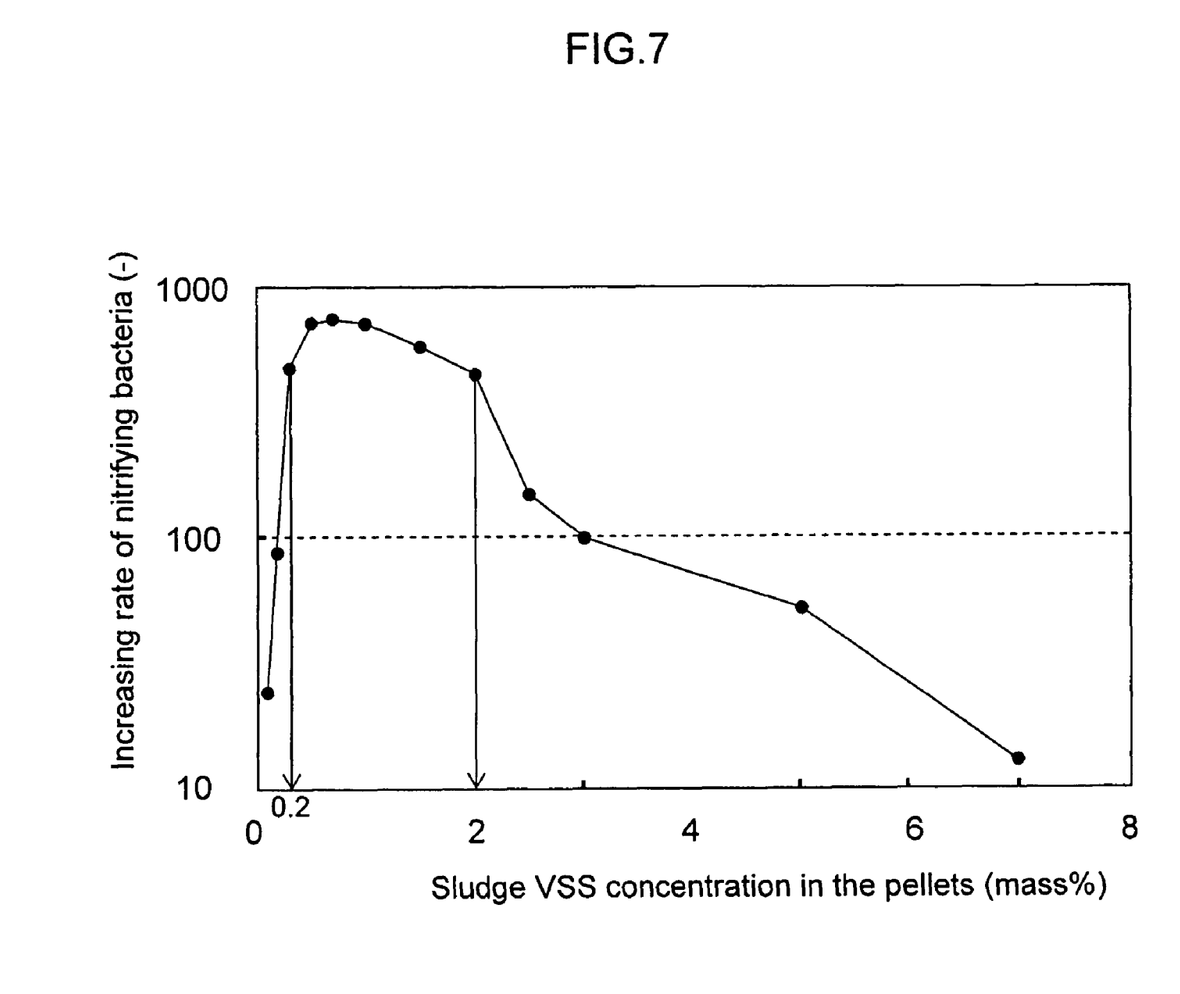
FIG. 7 is a graph in the present example.

As shown in FIG. 7, when the pellets contained the purified water sludge for a VSS concentration of 0.2 weight % to 2 weight %, the number of nitrifying bacteria was increased by about 500 fold, meaning that the increasing rate of nitrifying bacteria was high. Further, when the pellets contained the purified water sludge for a VSS concentration of 0.5 weight % to 1 weight %, the number of nitrifying bacteria was increased by about 1,000 fold, meaning that the increasing rate of nitrifying bacteria was higher.

Presumably, a reason for this is that, when the pellets contained the purified water sludge for a VSS concentration of less than 0.2 weight %, it is difficult to grow microorganisms coexisting with nitrifying bacteria in the pellets, and toxin caused by growth of nitrifying bacteria cannot be sufficiently reduced. It is also assumed that, when the pellets contained the purified water sludge for a VSS concentration of more than 2 weight %, heterotrophic bacteria easily oxidize organic substances and the amount of dissolved oxygen used for nitrification reaction is insufficient, making it difficult to grow nitrifying bacteria.

What is claimed is:

1. Pellets, comprising entrapped and immobilized sludge containing nitrifying bacteria, the sludge obtained from purifying water
wherein:
the entrapped and immobilized sludge has a VSS/SS ratio of 0.1 to 0.3, a VSS concentration of 0.2 weight % to 2 weight %, an SS concentration of 2 weight % or more, and an average particle size of 10 μm to 30 μm.

2. Wastewater treatment equipment, comprising:
the pellets according to claim 1 in a treatment tank.

3. A wastewater treatment process, comprising:
introducing the pellets according to claim 1 into a treatment tank to treat wastewater.

* * * * *